United States Patent [19]

Wolfinbarger

[11] Patent Number: 5,556,379
[45] Date of Patent: Sep. 17, 1996

[54] PROCESS FOR CLEANING LARGE BONE GRAFTS AND BONE GRAFTS PRODUCED THEREBY

[75] Inventor: Lloyd Wolfinbarger, Norfolk, Va.

[73] Assignee: Lifenet Research Foundation, Virginia Beach, Va.

[21] Appl. No.: 395,113

[22] Filed: Feb. 27, 1995

Related U.S. Application Data

[63] Continuation-in-part of Ser. No. 293,206, Aug. 19, 1994, abandoned.

[51] Int. Cl.$^6$ ............................................. A61M 31/00
[52] U.S. Cl. .............................. 604/49; 128/898; 623/16
[58] Field of Search .......................... 128/898; 604/28, 604/48, 49; 600/36; 623/16; 435/1, 267, 268

[56] References Cited

U.S. PATENT DOCUMENTS

| | | |
|---|---|---|
| 4,020,183 | 4/1977 | Asculai et al. . |
| 4,169,123 | 9/1979 | Moore et al. . |
| 4,207,689 | 6/1980 | Romera-Sierra et al. . |
| 4,258,722 | 3/1981 | Sessions et al. . |
| 4,315,919 | 2/1982 | Shanbrom . |
| 4,366,822 | 1/1983 | Altshuler . |
| 4,412,985 | 11/1983 | Shanbrom . |
| 4,456,589 | 6/1984 | Holman et al. . |
| 4,526,751 | 7/1985 | Gartner . |
| 4,553,974 | 11/1985 | Dewanjee . |
| 4,637,931 | 1/1987 | Schmitz . |
| 4,678,470 | 7/1987 | Nashef et al. . |
| 4,695,536 | 9/1987 | Lindstrom et al. . |
| 4,801,299 | 1/1989 | Brendel et al. . |
| 4,891,221 | 1/1990 | Shanborm . |
| 4,923,677 | 5/1990 | Simon et al. . |
| 4,946,792 | 8/1990 | O'Leary . |
| 4,975,526 | 12/1990 | Kuberasampath et al. . |
| 4,994,030 | 2/1991 | Glowczewakie Jr. et al. . |
| 5,037,437 | 8/1991 | Matsen, III . |
| 5,041,055 | 8/1991 | Roth . |
| 5,047,030 | 9/1991 | Draenert . |
| 5,106,626 | 4/1992 | Parsons et al. . |
| 5,118,512 | 6/1992 | O'Leary et al. . |
| 5,120,656 | 6/1992 | O'Leary et al. . |
| 5,133,756 | 7/1992 | Bauer et al. . |
| 5,167,961 | 12/1992 | Lussi et al. . |
| 5,186,945 | 2/1993 | Shanbrom . |
| 5,192,282 | 3/1993 | Draenert ................................ 606/65 |
| 5,333,626 | 8/1994 | Morse et al. . |
| 5,454,815 | 10/1995 | Geisser et al. ........................ 606/85 |

FOREIGN PATENT DOCUMENTS

| | | |
|---|---|---|
| 952189 | 8/1982 | U.S.S.R. . |
| 964545 | 7/1964 | United Kingdom . |

OTHER PUBLICATIONS

Helenius, A. et al. "Solubilization of Membranes by Detergents," Biochim. Biophys, Acta 415 (1975).

(List continued on next page.)

*Primary Examiner*—Randall L. Green
*Assistant Examiner*—V. Alexander
*Attorney, Agent, or Firm*—Klima & Hopkins, P.C.

[57] ABSTRACT

A process for removing substantially all bone marrow from a large bone and a bone graft produced thereby. A large substantially intact bone is selected and excess cartilage is removed from at least one articulating surface of the bone. An opening is prepared through the cortical layer of the bone to permit access of a vacuum line to the bone cavity. A vacuum line is attached to the bone via the opening for application of vacuum to the bone cavity, and the opening is sealed. A vacuum is applied to draw a first cleaning solution through the bone cavity so as to draw the first solution and solubilized bone marrow through the vacuum line to exit the bone at the opening. The vacuum is discontinued when the bone has been substantially cleaned of bone marrow. Subsequently, a second flushing solution may be drawn through the bone cavity via vacuum.

58 Claims, 6 Drawing Sheets

OTHER PUBLICATIONS

Sattar et al., "Survival and Disinfectant Inactivation of the Human Immunodeficiency Virus: A Critical Review", RID 1991; 13 (May–Jun.), pp. 430–447.

Exact, excerpts from "Product Specifications, Discription, Patent Application & Supporting Documentation", by EXOxEmis Inc., Feb. 1991.

Klebanoff et al., "Virucidal Activity of H202–generating Bacteria: Requirement for Peroxidase and Halide", Dept. of Medicine, University of Washington School of Medicine, Seattle, Washington, Sep. 24, 1973.

"DMIN Aseptic Tissue Demineralization", a product brochure from Osteotech, Inc. 1993.

"Maximum Security for You and Your Patient", a product brochure regarding VIP Bone, from Cryolife Inc., Feb. 12, 1992.

"The Virucidal Capacity of a Surfactant/Iodophor–Based Viral Inactivation Process for Bone Allografts" a report of studies designed and funded by Cryolife, Inc., undated.

Withrow et al., "Evaluation of the Antiretroviral Effect of Various Methods of Sterilizing/Preserving Corticocancellous Bone", presented at the 36th Annual Meeting, Orthopaedic Research Society, Feb. 5–8, 1990, New Orleans, Louisiana, Transactions of the Orthopaedic Research Society, 16, 1990, p. 226.

Garrison et al., "Comparison of Bacterial Contamination of Cadaveric Bone Allograft Collected Under Operating Room and Morgue Condition with and without the use of a Decontaminating Process", presented at The Second Congress of the European Association of Tissue Bank, Athens, Greece, May 1993.

Morse, "A New Surfactant/Iodophor–Based Viral Inactivation Process (VIP) for Preparation of Bone Allografts", presented at the 16th Annual Meeting of the American Association of Tissue Banks, San Diego, Aug, 1992.

"Improve Performance of Your Immunoassay Systems and Immunodiagnostic Kits", a product brochure by Medicine & Applied Sciences, Inc., undated.

"Viral Inactivation Agent for Blood Samples", an article referring to an Oct. 1990 issue of *American Clinical Laboratory* entitled An Antiviral Agent for General Use in Biological Samples.

*Virginia Tissue Bank Procedure Manual*, Section 5.9.4.5, Copyright registered on Aug. 6, 1986.

Buck et al., "Human Immunodeficiency Virus Cultured From Bone. Implications for Transplantation", Clinical Orthopaedics and Related Research, No. 251, 1990.

*Navy Tissue Bank, Tissue Bank Coordinator Manual, 10. "Procurement of Deep Tissues and Bones", p. 9, (undated).*

Shutkin, "Homologous–Serum Hepatitis following the Use of Refrigerated Bone–Bank Bone", The Journal of Bone and Joint Surgery, vol. 16–1, No. 1, 1954.

Hyatt et al., "Bone Grafting. The Procurement, Storage, and Clinical Use of Bone Homografts", The American Academy of Orthopaedic Surgeons, Ann Arbor, U.S.A., 1957.

"Transmission of HIV through Bone Transplantation: Case Report and Public Health Recommendations:", Morbidity and Mortality Weekly Report, vol. 37, No. 39, 1988.

Kakaiya et al., "Tissue Transplant–Transmitted Infections", Transfusion, vol. 31, No. 3, 1991.

Tomford et al., "A Study of the Clinical Incidence of Infections in the Use of Banked Allograft Bone", The Journal of Bone and Joint Surgery, vol. 63–A, No. 2, 1981.

Furlini et al., "Antibody Response to Human Immunodeficiency Virus after Infected Bone Marrow Transplant", Eur. J. Clin. Microbiol. Infect. Dist., vol. 7, 1988.

Lord et al., "Infection in Bone Allografts. Incidence, Nature, and Treatment", The Journal of Bone and Joint Surgery, vol. 70–A, No. 3, 1988.

Bonfiglio et al., "The Immune Concept: Its Relation To Bone Transplantation", Annals New York Academy of Sciences, 1955.

Doppelt et al., "Operational and Financial Aspects of A Hospital Bone Bank", The Journal of Bone and Joint Surgery, vol. 63–A, No. 9, 1981.

Dirschi et al., "Topical Antibiotic Irrigation in the Prophylaxis of Operative Wound Infections in Orthopedic Surgery", Orthopedic Infection, vol. 22, No. 3, Jul. 1991.

Reynolds et al., "Clinical Evaluation of the Merthiolate Bone Bank and Homogenous Bone Grafts", The Journal of Bone and Joint Surgery, vol. 33–A, No. 4, 1951.

"MED CLEAN MARK II", a product brochure by Advanced International Marketing for a unit which includes a pressurized stream of water for bone debridement. (undated).

U.S. Department of Health and Human Services/Public Health Service, "Transmission of HIV Through Bone Transplantation: Case Report and Public Health Recommendations", Morbidity and Morality Weekly Report, 37, 1988, pp. 597–599.

Mellonig, J. T. et al., "HIV Inactivation in a Bone Allograft", J. Periodontology, Dec. 1992, vol. 63, pp. 979–983.

Helenius, A. et al., "Solubilization of Membranes by Detergents", Biochim. Biophys. Acta 415 (1975) 29–79.

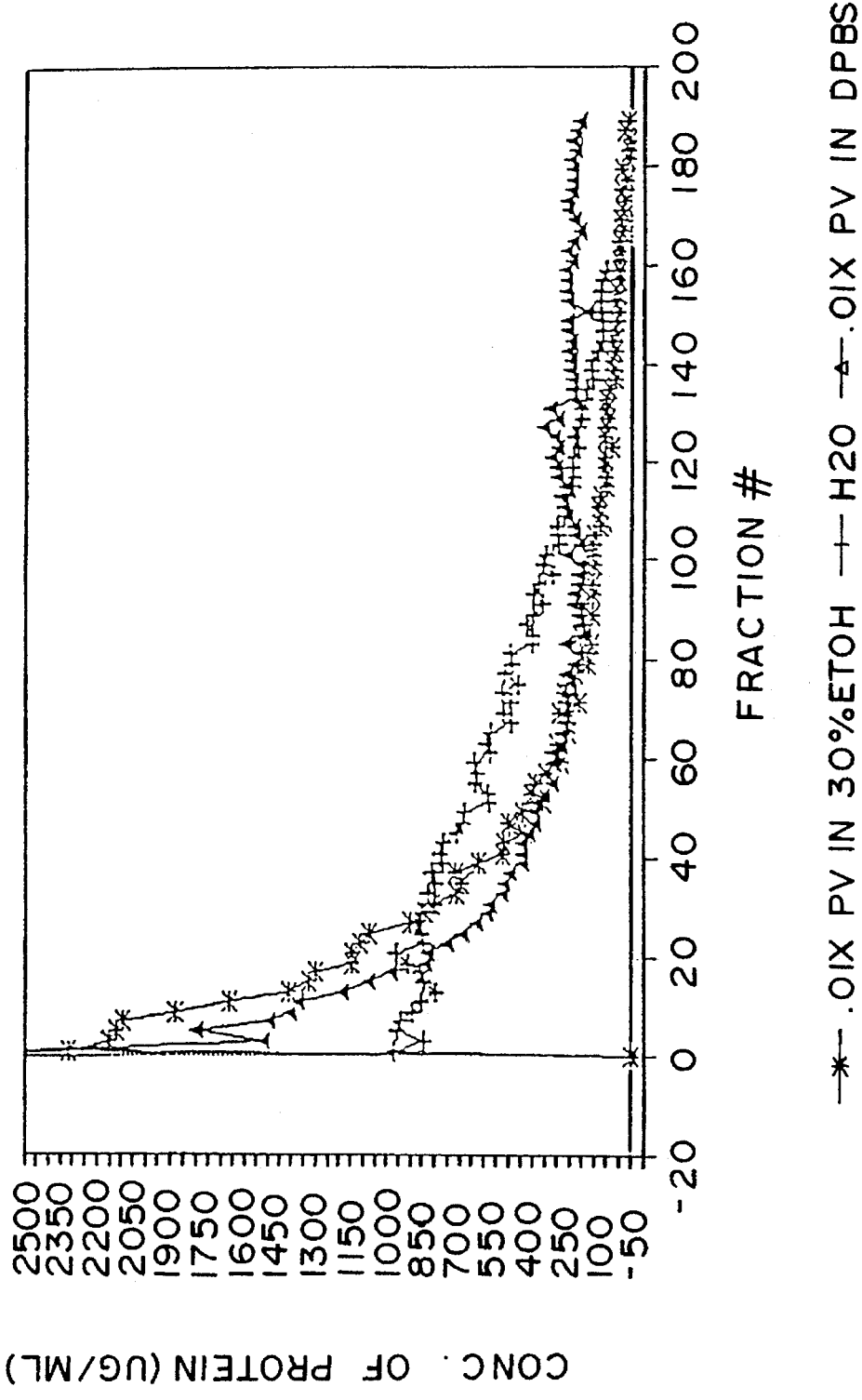

PROCESS FOR CLEANING LARGE BONE GRAFTS AND BONE GRAFTS PRODUCED THEREBY

REFERENCE TO RELATED APPLICATION

This application is a continuation-in-part of application Ser. No. 08/293,206, filed Aug. 19, 1994, now abandoned the disclosure of which is incorporated by reference in its entirety.

BACKGROUND OF THE INVENTION

1. Field of the Invention

This invention relates to a process for the cleaning of large bone grafts and bone grafts produced thereby. As used herein, a "large" bone graft is defined as one which is a substantial part of a whole bone and is easily recognizable as to its origin. Practically speaking, large bones, as defined herein may include the range of whole bones down to pieces at least as small as half of a whole bone and possibly as small as a third of a bone. The process possesses the attributes of being usable on a large number of bone grafts, including but not limited to femur, tibia, ilia, humerus, etc., prior to subsequent processing into specific grafts. The process is directed especially to human cadaveric bones, but is equally applicable to large bones obtained from other species.

The process involves the removal of bone marrow from the interstitial lumen and cancellous bone space by causing a flow of solvent through the cartilaginous ends of bone and out through the lumen and cancellous bone space by use of a vacuum. The solvent includes a combination of solutes which improve solvent penetration into and through the bone graft and increases the solubility of bone marrow, facilitating its removal from the large, essentially intact, bone graft.

2. Discussion of Background Information

Human bone obtained from cadaveric donors is typically procured under sterile conditions in an operating suite environment of local hospitals. The bone is stored frozen until it is further processed into small grafts under similar sterile conditions, or under clean-room conditions. Procurement and processing of human tissues is typically performed by groups certified by the American Association of Tissue Banks under standard operating procedures for the processing of each specific bone graft. Large bones such as the femur are thawed and debrided of excess tissue prior to being cut into smaller grafts.

Processing of the smaller grafts includes cleaning of bone marrow from the cancellous bone spaces using mechanical means, soaking, sonication, and/or lavage with pulsatile water flow under pressure. This cleaning may use reduced or elevated temperatures, for example 4° C. to 65° C., and may also include the use of detergents, alcohol, organic solvents or similar solutes or combination of solutes designed to facilitate solubilization of the bone marrow.

Although current donor screening protocols have been suggested to reduce the potential for transmission of the HIV virus through allograft tissues to less than one chance in from 1 to 10 million, the post procurement processing of allograft tissues is currently a manual process involving individual technician handling of the tissues. Since bone marrow represents the largest potential reservoir for any HIV virus present in an allograft bone tissue, it is expected that the process step of removal of bone marrow from the allograft bone tissues poses the greatest risk of transmission to the technician doing the processing. For example, a human femur may provide individual bone grafts consisting of portions of the bone shaft, femur head, proximal and/or distal femur grafts, and dividing the femur into these parts prior to removal of bone marrow increases the potential for process associated scattering of bone marrow elements within the processing room.

Bone marrow elements include hematopoietic progenitor cells, i.e., those stem cells that will ultimately differentiate into red blood cells, white blood cells, and platelets, among others. These stem cells are rich in major histocompatibility antigens (i.e., MHC antigens) that function in immune responses. Current processing techniques do not effectively remove bone marrow from the less solvent-accessible cancellous bone spaces within bone grafts, such as, for example, the trochanter portion or the femoral head area of the proximal femur, because current processing techniques rely upon soaking procedures which may or may not include agitation.

Typically, hydrogen peroxide is used to oxidize the colored elements within the bone marrow, which results in a cleaner appearance. However, such bone often still contains bone marrow which is extremely immunogenic.

Further, most bone grafts are currently stored in the freeze-dried state. Freeze-drying removes water from the grafts, but lipid elements present in the membranes of the bone marrow cells and in vesicle present in adipocytes (i.e., fat storage cells) typically leak from the grafts after being placed in their final storage and distribution containers. Thus, these residues often give the appearance that the graft itself is not clean.

Cleaning of bone marrow from small bone grafts has been described in the scientific literature and in brochures and documents made public by groups involved in the procurement and processing of human tissues. A for-profit public corporation, Cryolife, Inc. (Marietta, Georgia) promotes a bone cleaning process designated as VIP™ (Viral Inactivation Process) and claims that the process provides "Cleaner bone through mechanical removal of debris and tissue such as bone marrow, lipids and blood components" and "Safer bone through inactivation of pathogens such as HBV and HIV (greater than 5-log kill) as well as bacteria and fungi" (Cryolife Orthopedics, Inc. brochure 12 Feb., 1992; Cryolife literature directed to Organ and Tissue Procurement Program Directors dated Feb. 20, 1992).

Minimal information regarding the methods of the process is available but it is described as a multi-step approach having three phases: 1) preliminary surface disinfection of procured tissue for the protection of processing technicians during thawing, debriding and cutting; 2) cleaning and removal of debris from the cut pieces with a surfactant at elevated temperature; and 3) terminal disinfection of the cleaned bone grafts (The Virocidal Capacity of a Surfactant/ Iodophor-Based Viral Inactivation Process for Bone Allografts, Cryolife documentation). The VIP process is claimed to both clean bone allografts, e.g., a femur head, and to inactivate a variety of bacteria and viruses without affecting bone strength or biological properties. However, according to documents made public by Cryolife, Inc, the process is used to clean the surfaces of large bone grafts and to remove bone marrow from the cancellous bone spaces of small bone grafts cut from the larger grafts.

A second, for-profit publicly held corporation, Osteotech, Inc., Shrewsbury, New Jersey, describes a bone graft cleaning process called Permein™ ("a combination of ethanol and non-ionic detergent"; Mellonig, J. T., Prewett, A. B., and Moyer, M. P. J. Periodontol. December 1992, vol. 63, pp 979–983). This process involves the use of a solution of ethanol and detergent to clean bone grafts. Details of the process and detergents utilized are not currently available. Bone is soaked in the solution and it is claimed that the combination of ethanol and detergent facilitates permeation of the solution into bone. The process has been demonstrated to clean small cut-bone grafts and to be capable of inactivating the HIV in bone allograft (finely ground bone) (Mellonig, Prewett, and Moyer, J. Periodontology, December, 1992, 63: 979–983).

SUMMARY OF THE INVENTION

An object of the present invention is to provide a means of removing bone marrow from the luminal and cancellous bone spaces in large, essentially whole, bone grafts.

An object of the present invention is to provide large bone graft material which is essentially free of residual bone marrow, for use in the preparation of small bone grafts. Large, essentially whole, bone grafts with minimal residual bone marrow offer additional advantages in that removal of bone marrow, which may harbor potential viral particles and/or viral genomes integrated into the genomes of specific cell types present in the bone marrow, reduces the potential for transmission of infective agents such as bacteria and viruses, especially the human immunodeficiency virus (HIV), since cells capable of harboring the HIV virus are abundant in bone marrow. The removal of bone marrow from large, essentially whole, bone grafts also reduces the bioburden of viruses which may be present within the bone marrow cells removed.

Another object of the present invention is to provide cleaning procedures which permit removal of most or substantially all of the bone marrow elements from large bone grafts with minimal handling and processing, to reduce the risk of viral, bacterial and fungal transmission. The bone cleaning procedure according to the present invention results in the effective removal of substantially all of the bone marrow elements within the cancellous bone spaces of bone grafts.

Another object of this invention is to use alcoholic (for example, ethanol) and soluble amphiphile (i.e., detergent) solutions in the removal of bone marrow from bone grafts. Ethanol and detergents have been demonstrated to be viricidal towards enveloped viruses such as the HIV, hepatitis, and herpes viruses, for example. Further viruses which have been killed by compositions used in the instant invention include measles virus, togavirus, enterovirus, rhinovirus, rubella virus, reovirus, respiratory syncytial virus, cytomegalovirus, Epstein Barr Virus, Vesicular Stomatitis Virus, vaccinia virus, rabies virus, influenza virus, parainfluenza virus, adeno-associated virus, lymphoma virus, human papovirus, and lymphocytic choriomeningitis virus, for example. Ethanol and detergents have been demonstrated to be bacteriocidal toward certain bacteria, such as gonorrhea, gram negative bacteria, for example, *Yersinia enterocolitica*, gram positive bacteria, for example *Myobacterium tuberculosis* and Chlamydia, as well as acid fast bacteria.

Alcohol and detergent solutions also offer advantages of enhancing solubilization of bone marrow, reducing surface tension properties of aqueous solutions, and inactivating viruses and bacteria.

A further object of this invention is to provide methods for removing bone marrow from bone grafts prior to their being cut into smaller bone grafts. Thus, the present invention provides a process for cleaning large bone grafts which includes selecting a large substantially intact bone, and applying a vacuum to draw solution comprising at least one solvent for bone marrow through the large substantially intact bone to solubilize bone marrow.

The use of vacuum induced flow of solvent through the bone grafts offers the advantages of reducing the solubility of dissolved air in the fluid present within the bone marrow, of causing a movement of solvent solubilized bone marrow in the direction of the vacuum source, of minimizing structural damage to the cancellous bone by using minimally invasive clearing methods, and of permitting containment of the aspirated bone marrow/solvent in containers which may be safely handled and disposed without exposure to the processing personnel.

Use of hypotonic solutions induces bone marrow cell swelling and the partial vacuum reduces the solubility of dissolved air in the fluid present in the bone. Thus, with vacuum application to the bone, dissolved air comes out of solution forming gas bubbles which, if formed within cells in the bone marrow, will enhance rupture of the already swollen cells, with subsequent loss of cytoplasmic materials, and fragmentation and solubilization of cells.

The movement of solvent in the direction of the vacuum source will result in the continual exchange of solvent with the result that solubilized bone marrow is removed and bone marrow which has not been solubilized will be exposed to additional fresh solvent. Thus, the continual replacement of solvent will reduce the need for greater concentrations of solubilization enhancing components.

Detergents are amphiphile compounds which facilitate solubilization of relatively insoluble lipids present in, for example, bone marrow, yet at higher concentrations tend to form micellar structures (Helenius, A. and Simons, K. Solubilization of Membranes by Detergents, Biochim. Biophys. Acta 415 (1975) 29–79). The formation of micellar structures tends to limit the effective concentration range for detergent solutions, and thus, soaking of bone in a given volume of detergent solution may not be totally effective in that the absolute amount of detergent present is limited and if the amount of lipid material to be solubilized exceeds the solubilization capability of the detergent present, lipid solubilization will not be complete. By continually changing the detergent solution over time, it becomes possible to completely solubilize all solubilizable lipid present in a bone graft.

Restricted flow of solvent through the cartilaginous ends of the bone minimizes mechanical and/or structural damage to the cancellous bone by causing a slow flow rate of solvent through the trabecular bone space occupied by bone marrow. The containment of aspirated bone marrow/solvent is made possible by use of disposable containers for collection of the aspirate. In addition, it becomes possible to add strong viral/bacterial inactivators, such as sodium hypochlorite, for example, to the disposable collection containers to further inactivate potential pathogenic and/or biohazardous biomaterials.

Filters between the vacuum source and the collection containers further prevent the potential spread of biohazardous materials. The use of more traditional flushing procedures to remove bone marrow involves the use of pressurized flow of solution as a rapidly moving stream which dislodges bone marrow by impact of the solvent on the bone graft. Such procedures tend to generate aerosols of tissue and solvent which can be hazardous to processing personnel. The present invention virtually eliminates this hazard.

A yet further object of the invention is to provide mechanical devices which permit attachment of vacuum lines to the various large bone grafts being cleaned by the process of vacuum induced solvent flow, which permit attachment of the solvent containers around the bone grafts being cleaned, and to permit the collection and containment of aspirate materials from the bone grafts. These mechanical devices can be sterilized by a variety of procedures, for example, autoclaving, and form tight seals with the bone grafts being cleaned.

Still another object of the present invention is to provide a process for cleaning large bone grafts, which includes selecting a large substantially intact bone; removing excess cartilage from at least one articulating surface of the bone; optionally removing luminal bone marrow by mechanical and/or pulsatile flow means; preparing an opening through the cortical layer of the bone to permit access of a vacuum line to the bone cavity; attaching a vacuum line via the opening for application of vacuum to the bone cavity; sealing the opening; submersing the bone in a container of solution which contains one or more solvents for bone marrow; applying a vacuum to the vacuum line to draw the solution through the at least one cartilaginous articulating surface and then through the bone cavity so as to draw the solution and solubilized bone marrow through the vacuum line to exit the bone at the opening; and discontinuing the application of vacuum when the bone has been substantially cleaned of bone marrow.

Further, the process preferably includes refilling the container with a second solution for further processing the bone including flushing the first solution from the bone; and drawing the second solution through the at least one cartilaginous articulating surface and then through the bone cavity and the vacuum line to exit the bone at the opening.

Still further, the process preferably includes collecting the solution drawn through the bone cavity via the vacuum into a disposable container. Also, at least one strong viral or bacterial inactivator may be added to the disposable container prior to receiving solutions therein, to further reduce the risk of viral, bacterial or fungal transmission.

To still further reduce transmission risk, at least one filter may be provided in the vacuum line to further prevent the potential spread of biohazardous materials.

The process step of preparing an opening through the cortical layer may include drilling a hole through the cortical layer and optionally using pulsatile lavage for initial removal of bone marrow; sealing a tapping port in the drilled hole; and the step of attaching the vacuum line via the opening for application of vacuum to the bone cavity may include securely attaching one end of the vacuum line to the tapping port so as to seal the vacuum line with the cortical bone opening.

Alternatively, the process step of preparing an opening through the cortical layer may include cutting the bone transversely between proximal and distal ends, and preferably substantially in half; and the step of sealing the opening may include placing and sealing a sealing cap over the cut end of the bone; wherein the step of attaching the vacuum line via the opening for application of vacuum to the bone cavity may include securely attaching one end of the vacuum line to the sealing cap.

Additionally, the process may further optionally include initial removal of bone marrow from the cut end of the luminal space of the bone, using mechanical means and/or pulsatile lavage, prior to the steps of sealing the opening and attaching the vacuum line.

Further optionally, the container of the process may be a deformable container, and, after submersing the bone in the deformable container of solution, the process may further include tightly sealing the deformable container around the vacuum line or point of attachment of the vacuum line to the bone.

Preferably, the process according to the present invention includes adjusting the level of the applied vacuum to maintain solvent flow through the bone of from about 8 ml/min to 32 ml/min. More preferably, the applied vacuum is adjusted to maintain solvent flow through the bone of from about 15 ml/min to 25 ml/min.

Preferably, the first or cleaning solution includes endotoxin-free deionized/distilled water and at least one solvent selected from the group consisting of anionic detergents and non-anionic detergents. Optionally, the solution may include an alcohol, such as ethanol and isopropanol. Preferably, the solution comprises at least one solvent selected from the group consisting of polyoxyethylene alcohols, polyethylene glycol p-isooctylphenylethers, polyoxyethylene nonylphenol, and polyoxyethylene sorbitol esters. More preferably, the solution comprises a solution of Allowash solution (formerly referred to as Panavirocide in parent application Ser. No. 08/293,206, filed Aug. 19, 1994, now abandoned, and available from LifeNet Research Foundation, 5809 Ward Court, Virginia Beach, Va. Allowash solution comprises a solution of three detergents, i.e., (1) Brij-35 (more specifically, polyoxyethylene-4-lauryl ether having the chemical formula $C_9H_{19}(OCH_2CH_2)_4OH$), (2) Nonidet P-40 having the chemical name octylphenol-ethyleneoxide and also referred to as Tergitol NP-40, and sometimes referred to as NP-40, and (3) Nonoxynol-9 having the chemical name poly(ethylene glycol)p-nonyl-phenyl-ether.

The cleaning solution can comprise about 0.0001X to 10X of a 1X detergent solution containing about 0.066 weight percent Brij-35, about 0.02 weight percent Nonidet P-40, and about 0.02 weight percent Nonoxynol-9 in endotoxin free water, preferably, about 0.001X to 0.1X of the 1X detergent solution, more preferably, about 0.001X to 0.01X of the 1X detergent solution, and, most preferably, about 0.005X to 0.01X of the 1X detergent solution.

Still further, the cleaning solution can comprise a first solution comprising about 0.01X of the 1X detergent solution, and the process can comprise refilling the container with a second solution for further processing the bone including flushing the first solution from the bone; and drawing the second solution through the at least one cartilaginous articulating surface and then through the bone cavity and the vacuum line to exit the bone at the opening so that a maximum concentration of solution in the bone is equivalent to 0.001X detergent solution.

Alcohol, when included, is included in a solution of about 5 to 95% alcohol, measured by a volume-to-volume ratio, more preferably in the range of about 10 to 30% alcohol, measured by a volume-to-volume ratio. Preferred alcohols are ethanol and isopropanol.

The concentration of the at least one detergent in the cleaning solution ranges from about 0.001 to 2 weight percent, more preferably from about 0.01 to 0.5 weight percent.

Preferably, the first or cleaning solution is controlled within a temperature range of about 20° C. to 65° C. and maintained within the temperature range during processing. More preferably, the temperature range is controlled and maintained at about 27° C. to 55° C. Even more preferably, the temperature range is controlled and maintained at about 40° C. to 48° C.

Further preferably, the deformable container of solution which contains the bone is immersed into a temperature controlled water bath, for more stable temperature control.

The process according to the instant invention may also include monitoring the solution exiting the bone cavity to determine when essentially all of the bone marrow has been removed from the bone. Monitoring methods include, but are not limited to, measuring absorbance substantially at 410 nm, and visual monitoring of the color of the solution exiting the bone.

The second solution used in the process according to the instant invention includes a washing solution for flushing the first solution from the bone and for further reducing bacterial, fungal or viral contaminants. The washing solution includes at least one component selected from the group consisting of endotoxin-free deionized/distilled water and an alcohol, such as ethanol. Further, the washing solution includes at least one component selected from the group consisting of antibiotics, antiviral agents, hydrogen peroxide, permeation enhancers, organic acids and dilute solutions of strong acids.

Further, the first or cleaning solution may include at least one component selected from the group consisting of antibiotics, antiviral agents, hydrogen peroxide, permeation enhancers, organic acids and dilute solutions of strong acids.

The present invention also includes bone grafts produced by the process steps described above.

Another preferred process for cleaning large bone grafts according to the present invention includes selecting a large substantially intact bone; removing excess cartilage from at least one articulating surface of the bone; preparing an opening through the cortical layer of the bone by cutting the bone transversely between proximal and distal ends to permit access of a vacuum line to the bone cavity; submersing the bone in a deformable container of solution which contains one or more solvents for bone marrow; deforming ends of the deformable container around the cortical surface near the cut end of the bone; sealing the opening by placing and sealing a sealing cap over the cut end of the bone and the ends of the deformable container; attaching a vacuum line via the opening for application of vacuum to the bone cavity by securely attaching one end of the vacuum line to the sealing cap; applying a vacuum to through the vacuum line to draw the solution through the at least one cartilaginous articulating surface and then through the bone cavity so as to draw the solution and solubilized bone marrow through the vacuum line to exit the bone at the opening; and discontinuing the application of vacuum when the bone has been substantially cleaned of bone marrow.

Additionally, this process may further include refilling the deformable container with a second solution for further processing the bone including flushing the first solution from the bone; and drawing the second solution through the at least one cartilaginous articulating surface and then through the bone cavity and the vacuum line to exit the bone at the opening.

Preferably, the solution drawn through the bone cavity via the vacuum is collected into a disposable container. Further preferably, at least one strong viral or bacterial inactivator is included in the disposable container prior to receiving solutions therein. Still further, at least one filter may be provided in the vacuum line to further prevent the potential spread of biohazardous materials.

Optionally, the process may further include initial removal of bone marrow from the cut end of the luminal space of the bone, using pulsatile lavage, prior to the steps of sealing the opening and attaching the vacuum line.

Further optionally, the deformable container of solution which contains the bone may be immersed into a temperature controlled water bath, after attachment of the vacuum line, to more stably control the temperature of the solution.

The present invention also includes bone grafts produced by the process steps recited above.

BRIEF DESCRIPTION OF THE DRAWINGS

The present invention is further explained in the description which follows with reference to the drawings, illustrating, by way of non-limiting examples, various embodiments of the invention, with like reference numerals representing similar parts throughout the several views, and wherein:

FIG. 8 is a graph showing changes in absorbance of solution per volume of detergent drawn through a large bone sample according to the present invention.

DETAILED DESCRIPTION OF THE PREFERRED EMBODIMENTS

The process of the instant invention is carried out in a highly reproducible fashion, for consistent results in the formation of large bone graft material which is essentially free of residual bone marrow, for use in the preparation of small bone grafts. In a preferred embodiment, the process for cleaning large, essentially whole, bone grafts involves the thawing of bone materials procured from cadaveric donors. Following thawing under sterile conditions at room temperature, the bone is debrided of external soft tissues. This debridement includes removal of excess cartilaginous tissues on the proximal and distal ends of bones at their articulation surfaces 11, as shown in FIG. 1, for example.

Figure 1:
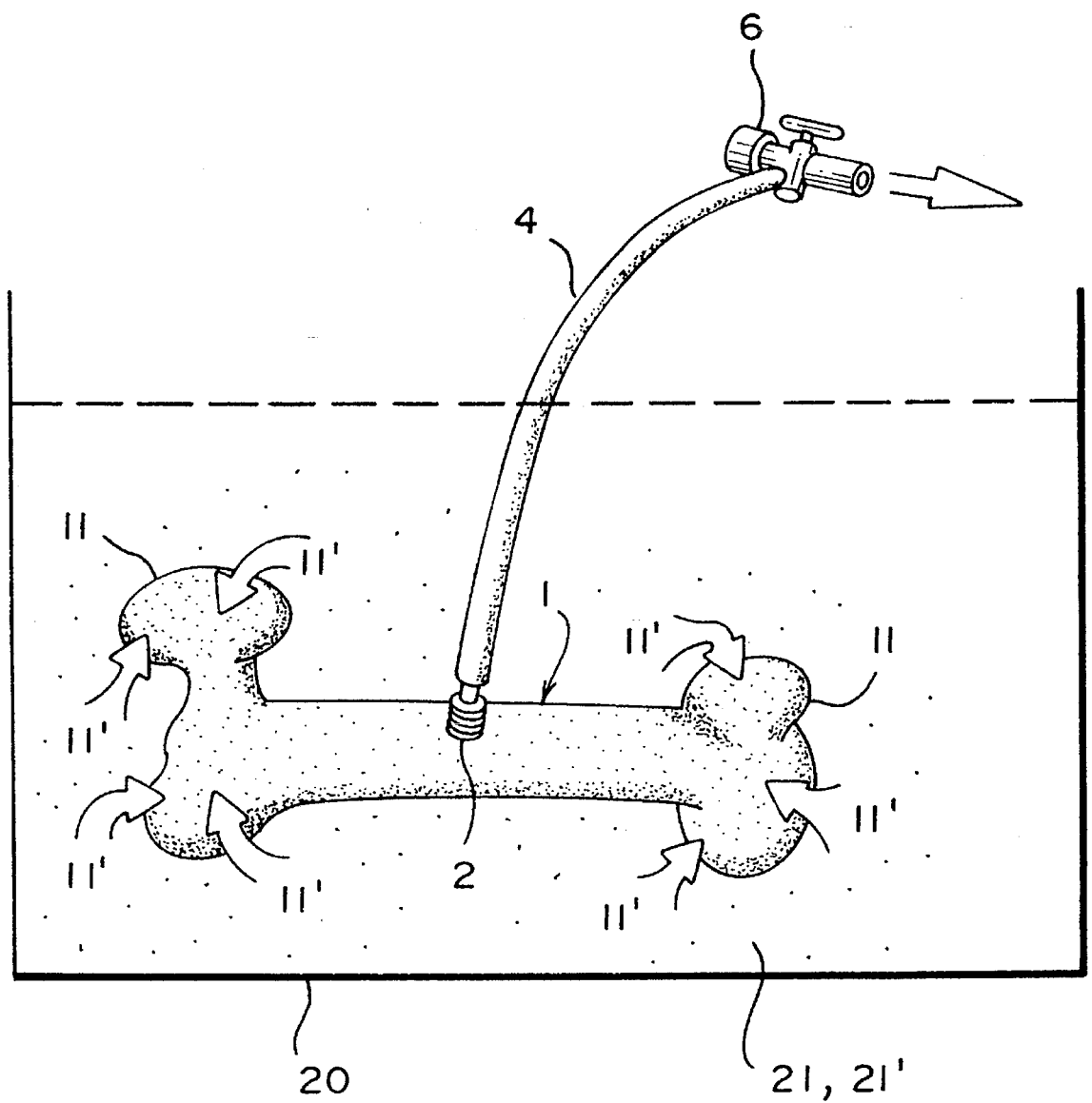
FIG. 1 is a plan view of an essentially whole femur being processed according to a preferred embodiment of the instant invention.

After debridement, one embodiment of the invention includes the formation of a hole 2 substantially midway between the distal and proximal ends of the bone 1, see FIG. 1. Hole 2 is preferably formed by drilling, and is preferably formed to have an outside diameter of approximately ¼ to ⅝ inch. The hole need only be drilled deep enough to penetrate the cortical bone to enable a tapping port 3 to be securely inserted into hole 2. After removing as much bone marrow as possible, a vacuum line 4 is attached securely at one end to the tapping port 3 after insertion of the tapping port 3 into hole 2.

Figure 6:
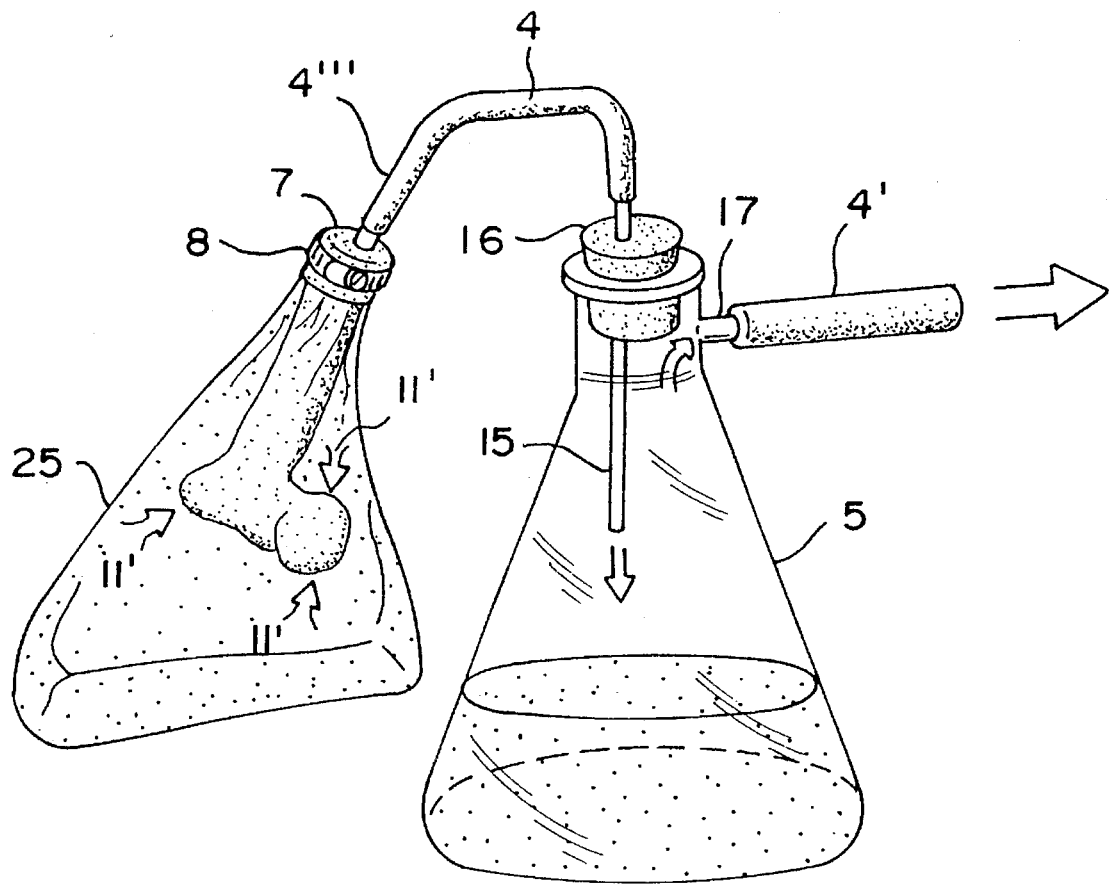
FIG. 6 is a plan view of an embodiment of a disposable container for collecting solutions drawn through a large bone graft. The disposable container of FIG. 6 is connected to a large bone graft as shown in FIG. 5, for example.

The opposite end of vacuum line 4 is securely attached to a disposable container 5, an example of which is shown in FIG. 6, via inlet tube 15. Inlet tube 15 is sealingly connected to disposable container 5 by stopper means 16. Stopper means 16 is preferably a rubber stopper, but any equivalent, such as, a cork stopper, may be used to seal inlet tube 15 within disposable container 5.

Outlet tube 17 of disposable container 5 is securely attached to another vacuum line 4'. At the opposite end, vacuum line 4' is attached to a vacuum source which is capable of drawing a vacuum in the range of about 5 mm to 60 mm Hg on the entire apparatus. The vacuum source used to draw solution through the bone grafts will be set to draw a vacuum between about 15 and 35 mm Hg with the preferred range being between about 20 and 30 mm Hg.

After connection of the vacuum apparatus, bone 1 is immersed into a solvent containing solution 21 contained within an open container 20. The vacuum source is next turned on to draw solution 21 through the articulation surfaces 11 which have been debrided of cartilage, through the cancellous bone structure and through the intermedullary canal of bone 1. The solution enters the bone generally along the flow paths indicated by the reference numeral 11'. As mentioned above, the vacuum drawn is set between about 15 and 35 mm Hg with the preferred range being between about 20 and 30 mm Hg. The actual vacuum level is adjusted such that the flow rate of solution through the bone graft does not occur so rapidly that the bone marrow is not effectively solubilized, but rapidly enough to effectively remove solubilized bone marrow. Flow rates of solvent should range between about 8 and 32 ml per minute with the preferred rates being between about 15 and 25 ml per minute.

The solvent containing solution 21 enters the bone 1 through the ends at the cartilaginous surfaces 11. Restricted flow of the solvent 21 through the cartilaginous ends 11 of the bone 1 minimizes mechanical and/or structural damage to the cancellous bone by causing a slow flow rate of solvent through the trabecular bone space occupied by bone marrow. As solvent containing solution 21 is drawn through the bone 1, it is collected in the disposable container 5 via the route indicated by the arrows in FIG. 6. Because the aspirate solution is largely liquid phase, as discussed previously, the solution is deposited into the disposable container as the vacuum is drawn through the inlet tube 15 and out the outlet tube 17.

Figure 7:
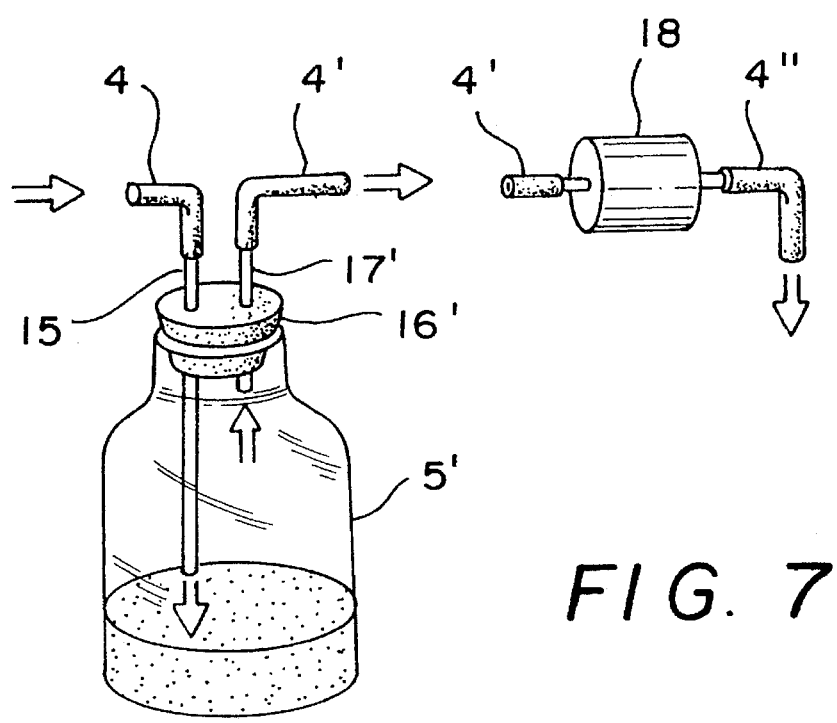
FIG. 7 is a plan view of another embodiment of a disposable container for collecting solutions drawn through a large bone graft.

Optionally, one or more air filters may be provided in the vacuum line between the disposable container and the vacuum source, as further assurance of prevention of contamination by airborne viruses/bacteria. As shown in FIG. 7, an air filter 18 may be provided which may be securely attached between two ends of a pair of vacuum lines 4' and 4".

FIG. 7 also shows an alternative embodiment of a disposable container. In this embodiment, both inlet tube 15 and outlet tube 17' are sealingly connected to disposable container 5' by stopper means 16'. Stopper means 16' is preferably a rubber stopper, but any equivalent, such as, a cork stopper, may be used to seal inlet tube 15 and outlet tube 17' within disposable container 5'.

Initially, upon immersion of the bone 1 into container 20, the container 20 contains a cleaning solution of a sterile mixture of at least one detergent in endotoxin-free deionized/distilled water. Optionally, the cleaning solution may also include an alcohol, such as ethanol. Detergents utilized may include various detergents, such as anionic detergents, non-anionic detergents, and combinations thereof. Examples of acceptable detergents are: polyoxyethylene alcohols (Brij series, Lubrol W, etc.), polyethylene glycol p-isooctylphenylethers (Triton X series), polyoxyethylene sorbitol esters (Tween series, Emasol series), in concentrations ranging between about 0.001 weight percent to 2 weight percent with the preferred concentrations being between about 0.01 and 0.5 weight percent.

Detergents are typically evaluated based on their "critical micelle concentration" (CMC). The CMC is that concentration of detergent in solution where free molecules of detergent begin to aggregate into micellar structures. The concentration of detergent that is utilized in the cleaning solution preferably includes concentrations of at least one detergent that exceeds the CMC so that there is sufficient detergent available in the solution to have micelles present in the solution to replenish monomeric detergent as it is consumed in bone marrow solubilization.

Moreover, cleaning solutions used in the present invention should be non-toxic and/or leave a non-toxic residual concentration of materials in the bone after flushing with the second solution. In particular, following cleaning of bone grafts, it is necessary that residual detergents which may remain associated with the bone graft are not toxic towards human fibroblast cells expected to migrate into the bone graft material(s) following implantation.

Preferred detergents include the formulations known as ALLOWASH™ solution (available from LifeNet Research Foundation, Virginia Beach, Va.) which comprise solutions of polyoxyethylene-4-lauryl ether (Brij-35), octylphenolethyleneoxide (Nonidet P-40), and poly(ethylene glycol)p-nonyl-phenyl-ether (Nonoxynol-9). For Brij-35, the published CMC is approximately 0.092 mM (millimolar) and was experimentally determined (by detergent mediated solubilization of an "insoluble" dye) to be about $0.120 \pm 0.026$ mM; for Nonoxynol 9, the published CMC is approximately 0.0812 mM and was experimentally determined to be about $0.062 \pm 0.008$ mM; and for Nonidet P-40, the published CMC is approximately 0.11 to 0.29 mM and was experimentally determined to be about $0.234 \pm 0.005$ mM.

A 1X solution of Allowash solution contains about 0.066 weight percent Brij-35, about 0.02 weight percent Nonidet P-40, and about 0.02 weight percent Nonoxynol-9 in endotoxin free water. A 0.01X solution of Allowash solution comprises a solution of 1 ml of the 1X solution in 99 ml of endotoxin free water, and other solutions comprise corresponding dilutions and/or concentrations thereof. For example, a 0.001X solution comprises a solution of 0.1 ml of the 1X solution in 99 ml of endotoxin free water to provide a solution comprising 0.0066 weight percent Brij-35, about 0.002 weight percent Nonidet P-40, and about 0.002 weight percent Nonoxynol-9 in endotoxin free water, and a 10X solution comprises 0.66 weight percent Brij-35, about 0.2 weight percent Nonidet P-40, and about 0.2 weight percent Nonoxynol-9 in endotoxin free water.

In accordance with the present invention, solutions can comprise concentrations of about 0.0001X to 10X, preferably 0.001X to 0.1X, more preferably 0.001X to 0.01X, and most preferably 0.005X to 0.01X. As discussed above, these solutions should preferably be at a concentration so that upon completion of cleaning of the bone, e.g., prior to implantation, the concentration of detergents and/or any of materials in the solution is below a toxic level. For example, a 0.01X solution is a preferred solution, because removal of 90 percent of this solution from the bone, such as by subsequent flushing with secondary solutions, reduces the concentration to approximately a 0.001X solution, which is the non-toxic level. Thus, a 0.01X solution provides a highly cost effective solution having an effective concentration of detergents without wasting excess detergents.

Formulations including solutions of detergents of Brij-35, Nonidet P-40, and Nonoxynol-9 are disclosed in. U.S. patent application Ser. No. 08/212,698, filed on Mar. 14, 1994, which discloses these formulations in combination with stabilizers so as to temporarily fix red blood cells thereby allowing sufficient time for the composition to inactivate viruses and bacteria while keeping red blood cells intact and undamaged. U.S. patent application Ser. No. 08/212,698 is hereby incorporated by reference in its entirety for its disclosure concerning detergents that are effective in reducing or killing microorganisms and viruses in a relatively short period of time.

The cleaning solutions of the present invention can include any extraneous components in amounts that are not detrimental to the cleaning of the bone. For example, components that may be a detrimental contaminant at higher concentrations can be non-toxic and/or without consequence to the cleaning efficiency of the cleaning solution at lower concentrations. Thus, for example, stabilizers, including glutaraldehyde and sucrose as disclosed in U.S. patent application Ser. No. 08/212,698, can be included in the cleaning solution in amounts that would not be detrimental to the cleaning ability of the cleaning solution and in amounts that would be non-toxic in the bone graft to be implanted.

The concentration of alcohol, such as ethanol, which may be used in the cleaning (i.e., first) solution ranges between about 5 and 95% (volume to volume) with the preferred range being between about 10 and 30% (volume to volume).

The temperature of the cleaning solution is adjusted and maintained within a controlled range of approximately 20° C. to 65° C. prior to addition of the bone 1, and the range is preferably within about 27° C. to 55° C. and most preferably within about 40° C. to 48° C. Additionally, the container 20 may be surrounded by a heated water bath (not shown) for maintaining a temperature range more stably and accurately. The heated water bath is maintained at substantially the same temperature range as the container 20 and cleaning solution 21.

The flow rate of first solution through the bone 1 is adjusted and maintained at a desired flow rate by controlling the amount of vacuum drawn by the vacuum source. The first solution is collected in the disposable container 5 and is initially dark red, reflecting a saturated or nearly saturated solution of marrow. As the process continues, the first solution gradually turns to a color similar to that of serum as bone marrow is removed from the graft. By sampling the effluent material (i.e., first solution) being removed from the bone 1, via a sampling port 6 accessible by use of a syringe, it is possible to monitor completion of bone marrow removal by measuring absorbance at 410 to 700 nm. By this method, it is possible to determine when essentially all of the bone marrow is removed from the bone graft. An example of the changes in absorbance of the solution exiting a bone per volume of detergent (i.e., Allowash solutions) is shown in the graph of FIG. 8. As illustrated in FIG. 8, bone marrow solubilization and cleaning of the bone is essentially complete when eluent protein concentration reaches a minimal, substantially stable value.

Other methods of determination of the degree to which the bone marrow has been removed from the bone graft include: taking core samples of bone plugs, solubilizing bone marrow in the bone plug core samples using sodium hydroxide and taking a protein assay of the same; visual inspection of the trabecular bone can be examined using a scanning electron microscope; and gross visual examination can be performed by cutting the graft open for visual inspection by the naked eye or with a stereoscope, for example.

After it has been determined that essentially all of the bone marrow has been removed from the bone 1 (i.e., the bone graft) the bone 1 is removed from the container 20 and the solution 21 is replaced with a second solution 21'. The bone is then immersed in the second solution 21' in the container, for further processing. The second solution to be drawn through the bone graft 1 may include endotoxin-free deionized/distilled water, alcoholic, e.g., ethanolic solutions of water, or isotonic saline in endotoxin-free deionized/distilled water. During addition of the second solution to the container, the vacuum can be shut off until processing of the second solution through the bone is ready to resume.

The second solution is drawn though the bone in order to reduce the amount of the first solution in the bone graft and/or to deliver additional agents to be used in processing of the whole bone graft. For example, addition of ethanol (50% to 100%, vol to vol) to the washing solution would serve to reduce bacterial, fungal and/or viral contaminants which might be present in the bone graft. The use of absolute (100%) ethanol in the second solution would further serve to dehydrate the bone, reducing subsequent times needed for freeze-drying.

Since the flow of solution through the bone graft will be less restricted during flushing with the second solution, the level of vacuum used is appropriately reduced to maintain an appropriate flow rate, preferably between 10 and 15 ml per minute.

The volume of the second solution which is drawn through the bone varies depending on the size of the bone being processed, the volume of the intermedullary canal of the bone being processed, and the concentration of detergent and/or alcohol used in the first solution, but in general should approximate a volume 10-fold greater than the volume of the bone graft being processed.

Following completion of flushing of the bone graft 1 with the second solution, the bone graft may be removed from the container and processed into smaller bone grafts via procedures previously established for the production of such grafts.

Optionally, one or more of the following components may be added to either or both of the first and second solutions being used to clean and flush t-he bone graft, respectively, including, but not limited to: antibiotics, antiviral agents (for example peroxide generating agents such as Exact [e.g., trademarked haloperoxidase products marketed by ExOx-Emis, Inc., San Antonio, Tex]), hydrogen peroxide, permeation enhancers (for example, fatty acid esters, such as laurate, myristate and stearate monoesters of polyethylene glycol), organic acids (for example, citric acid) or dilute solutions of strong acids (for example, hydrochloric acid).

Figure 2:
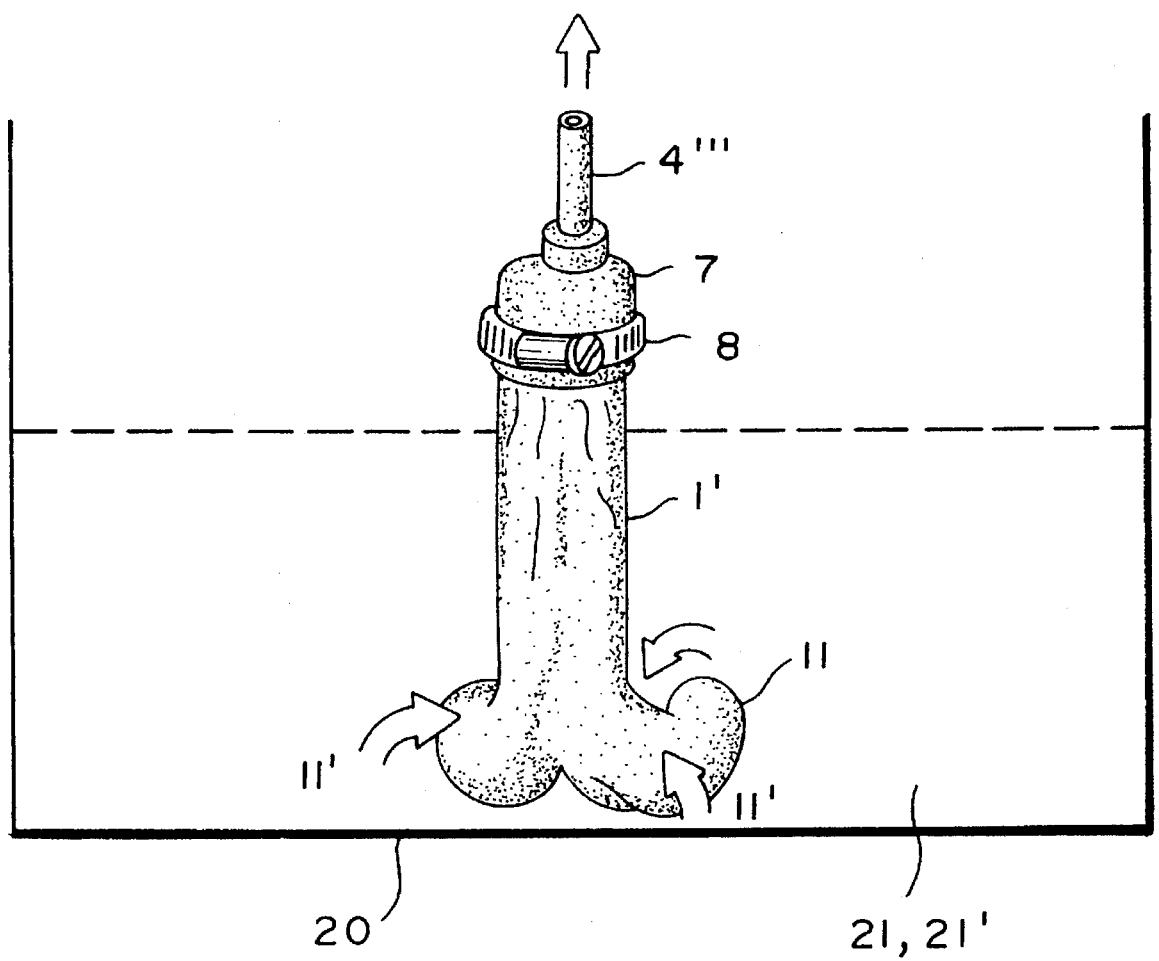
FIG. 2 is a plan view of a large bone graft, e.g. a half femur being processed according to a preferred embodiment of the instant invention.

FIG. 2 is a view of another embodiment of a bone cleaning apparatus and method. Those component/steps which are the same as in the embodiment shown in FIG. 1, have been labelled with the same reference numerals and may not be specifically described with respect to the instant embodiment. As described with regard to the embodiment shown in FIG. 1, a large bone is thawed and debrided of excess soft tissue (including the excess cartilage present on the articulating surfaces where desired). Next, the large bone is cut substantially in half approximately midway between its proximal and distal ends, using a bone saw. The distal end of the femur is shown in FIG. 2, for example. However, the proximal end of the femur, or either half of any of the previously mentioned large bones can be similarly processed. Optionally, pulsatile flow of sterile endotoxin-free water (e.g., Pulsavac lavage) may be used for initial removal of bone marrow from the luminal space, prior to vacuum processing.

A sealing cap 7 is placed over the cut end of the bone graft 1' and secured using a clamping device 8. Sealing cap 7 may be formed of rubber, plastic, or any equivalent material which is capable of forming a liquid and gas proof seal with both the bone graft 1' and the vacuum line 4. The sealing cap may be formed, for example, by injection molding, or other equivalent methods. The vacuum line 4 is attached securely to the access line 4''' in the sealing cap. The clamping device may be a metal or plastic hose clamp, nylon tie strap or other equivalent clamping mechanism.

The bone graft 1' is then attached to an apparatus and processed much in the same manner as described above with respect to the embodiment shown in FIG. 1.

Figure 3:
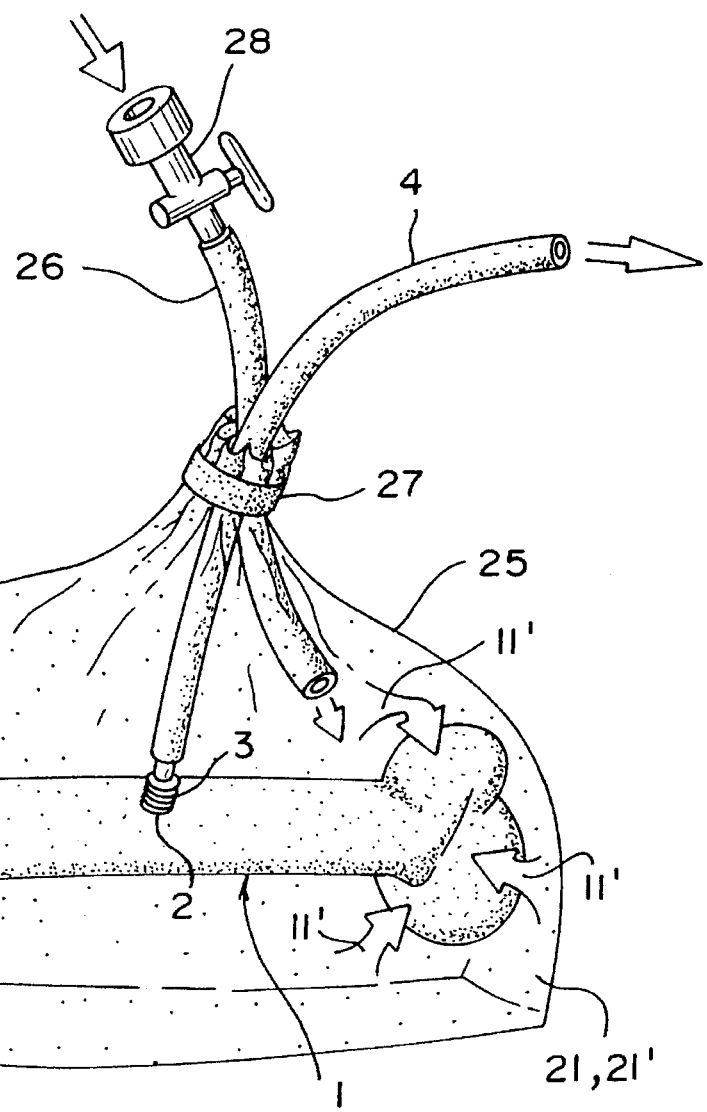
FIG. 3 is a plan view of an essentially whole femur being processed according to another embodiment of the instant invention.

FIG. 3 shows an essentially whole femur being processed according to another embodiment of the instant invention which is a variation of the process described with respect to FIG. 1. In this embodiment, the process for cleaning large, essentially whole, bone grafts involves thawing of the bone graft material under sterile conditions at room temperature, as described previously, after which the bone is debrided of external soft tissues, including cartilaginous tissues on the proximal and distal ends of bones at their articulation surfaces 11.

After debridement, a hole 2 is formed substantially midway between the distal and proximal ends of the bone 1, optionally, initial intramedullary removal of bone marrow is performed, and a vacuum line 4 is attached securely at one end to the tapping port 3 after insertion of the tapping port 3 into hole 2, much in the same manner as described with respect to FIG. 1. The opposite end of vacuum line 4 is securely attached to a vacuum source via a disposable container 5, in the same manner as that disclosed with respect to FIG. 6.

After connection of the vacuum apparatus, the bone 1 is immersed into a solvent containing solution 21 contained in a deformable container 25. The deformable container is preferably made of a plastic material such as polyethylene, but may be made of any suitably inert, flexible material such as polypropylene, for example. The deformable container 25 is then tightly sealed around the vacuum line 4 or point of attachment to the bone graft and, optionally, a filling tube 26, using sealing mechanism 27. Sealing mechanism 27 may be an elastic band, metal clamping device, string or other equivalent closure mechanism.

The vacuum source is next applied to draw solution 21 through the bone 1. As mentioned above, the vacuum drawn is set between about 15 and 35 mm Hg with the preferred range being between about 20 and 30 mm Hg. The actual vacuum level is adjusted such that the flow rate of solution through the bone graft does not occur so rapidly that the bone marrow is not effectively solubilized, but rapidly enough to effectively remove solubilized bone marrow. As solvent containing solution 21 is drawn through the bone 1, it is collected in the disposable container 5 via the route indicated by the arrow in FIG. 6.

The deformable container 25 provides an extra degree of safety as it substantially prevents any possibility of aerial transmission of viruses, bacteria or other vectors from the bone and through the solution bath, since the solution bath is essentially contained in a closed system.

Because the aspirate solution is largely liquid phase, as discussed previously, the solution is deposited into the disposable container as the vacuum is drawn through the inlet tube 15 and out the outlet tube 17.

Optionally, in the manner described above, one or more air filters may be provided in the vacuum line between the disposable container and the vacuum source, as further assurance of prevention of contamination by airborne viruses/bacteria and other vectors.

Initially, upon immersion of the bone 1 into deformable container 25, the deformable container 25 contains a cleaning solution of a sterile mixture of detergent in endotoxin-free deionized/distilled water, and, optionally, ethanol. Detergents utilized may include, but are not restricted to, those described above in the description of FIG. 1., in concentrations ranging between about 0.001 weight percent to 2 weight percent with the preferred concentrations being between about 0.01 and 0.5 weight percent. The temperature of the cleaning solution is adjusted and maintained within a controlled range, as discussed above.

The flow rate of first solution through the bone 1 is adjusted and maintained at a desired flow rate by controlling the amount of vacuum drawn by the vacuum source. The first solution is collected in the disposable container 5 and is initially dark red, reflecting a saturated or nearly saturated solution of marrow. As the process continues, the first solution gradually turns to a color similar to that of serum as bone marrow is removed from the graft.

As solvent is removed from the deformable container 25, the deformable container collapses around the bone graft 1, allowing the total volume of solution contained within the container 25 to be drawn through the bone graft. If after the total volume of the first solution is drawn through the bone graft, the bone graft still has not been sufficiently cleaned of bone marrow, additional amounts of first solution may be added to the deformable container.

The vacuum source is first turned off and then additional first solution may be added by opening filling port 28 and flowing solution into the deformable container through filling tube 26. When the desired amount of first solution has been added to the deformable container, the filling port is closed again to allow a vacuum to be drawn upon restart of the vacuum source. The vacuum source is restarted and the flow of first solution through the bone graft resumes until the bone graft has been sufficiently cleaned of bone marrow.

Although preferred, a filling tube need not be used to refill the deformable container. Instead, after turning off the vacuum source, the sealing mechanism 27 may be undone or loosened to allow the first solution to be poured directly into the opening of the deformable container 25.

After it has been determined that essentially all of the bone marrow has been removed from the bone 1 (i.e., the bone graft), the second solution is added to the deformable container in the same manner previously described for adding more of the first solution. If there is a volume of first solution remaining, the deformable container can be opened by loosening or removal of the sealing mechanism 27, after which the first solution is poured out of the deformable container, the second solution is added to the deformable container and the sealing mechanism is resealed for recommencement of vacuum processing with the second solution 21'. The second solution to be drawn through the bone graft 1 is the same as that described previously with regard to FIG. 1.

The second solution is drawn though the bone in order to reduce the amount of the first solution in the bone graft and/or to deliver additional agents to be used in processing of the whole bone graft. Since the flow of solution through the bone graft will be less restricted during flushing with the second solution, the level of vacuum used is appropriately reduced to maintain an appropriate flow rate, preferably between about 10 and 15 ml per minute.

The volume of the second solution which is drawn through the bone varies depending on the size of the bone being processed, the volume of the intermedullary canal of the bone being processed, and the concentration of detergent and/or alcohol used in the first solution, but in general should approximate a volume 10-fold greater than the volume of the bone graft being processed. As with the first solution, additional volumes of second solution may be added to the deformable container, as needed, either via the filling port 28 and filling tube 26, or by opening the deformable container via the sealing mechanism 27.

Following completion of flushing of the bone graft 1 with the second solution, the vacuum source is discontinued, the sealing mechanism 27 is released, the deformable bag is removed form the bone graft 1, the tapping port 3 is removed from the bone graft 1 and the bone graft may then be processed into smaller bone grafts via procedures previously established for the production of such grafts.

As with the previous embodiment, optionally, one or more of the following components may be added to either or both of the first and second solutions being used to clean and flush the bone graft, respectively, including, but not limited to: antibiotics, antiviral agents (for example peroxide generating agents such as Exact [a trademarked product marketed by ExOxEmis, Inc., San Antonio, Tex.]), hydrogen peroxide, permeation enhancers (for example fatty acid esters such as laurate, myristate and stearate monoesters of polyethylene glycol), organic acids (for example citric acid) or dilute solutions of strong acids (for example hydrochloric acid).

Figure 4:
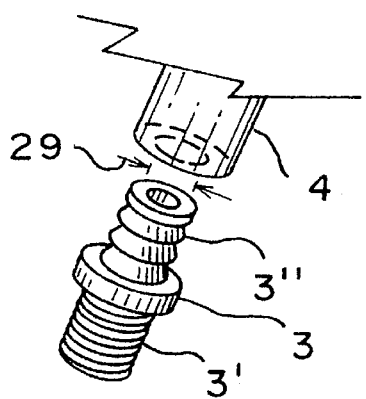
FIG. 4 is an enlarged view of a tapping port and connecting vacuum line according to a preferred embodiment of the instant invention.

FIG. 4 is an enlarged view of a preferred form of tapping port 3 for interconnecting the bone graft and vacuum line 4. Preferably, bottom port 3' is formed as a threaded cylinder and upper port 3" is formed as a conical section which expands in cross-section from the open end toward the center of the disk-shaped portion 3''' of the port 3. This expanding cross-section allows the vacuum line to be press fit onto the upper port 3' until the cross-section of the upper port 3' is greater than the inner diameter 29 of the vacuum line, to slightly expand the vacuum line and form a tight seal between the vacuum line and the upper port 3". The present invention is not to be limited to the specific port shown in FIG. 4, however, as other equivalent ports which are capable of providing a gas-tight seal between a vacuum line and a bone sample may be used. For example, a port having a threaded cylinder for connecting with a bone sample, and a smooth cylindrical port for being clamped within a vacuum line could be used.

Figure 5:
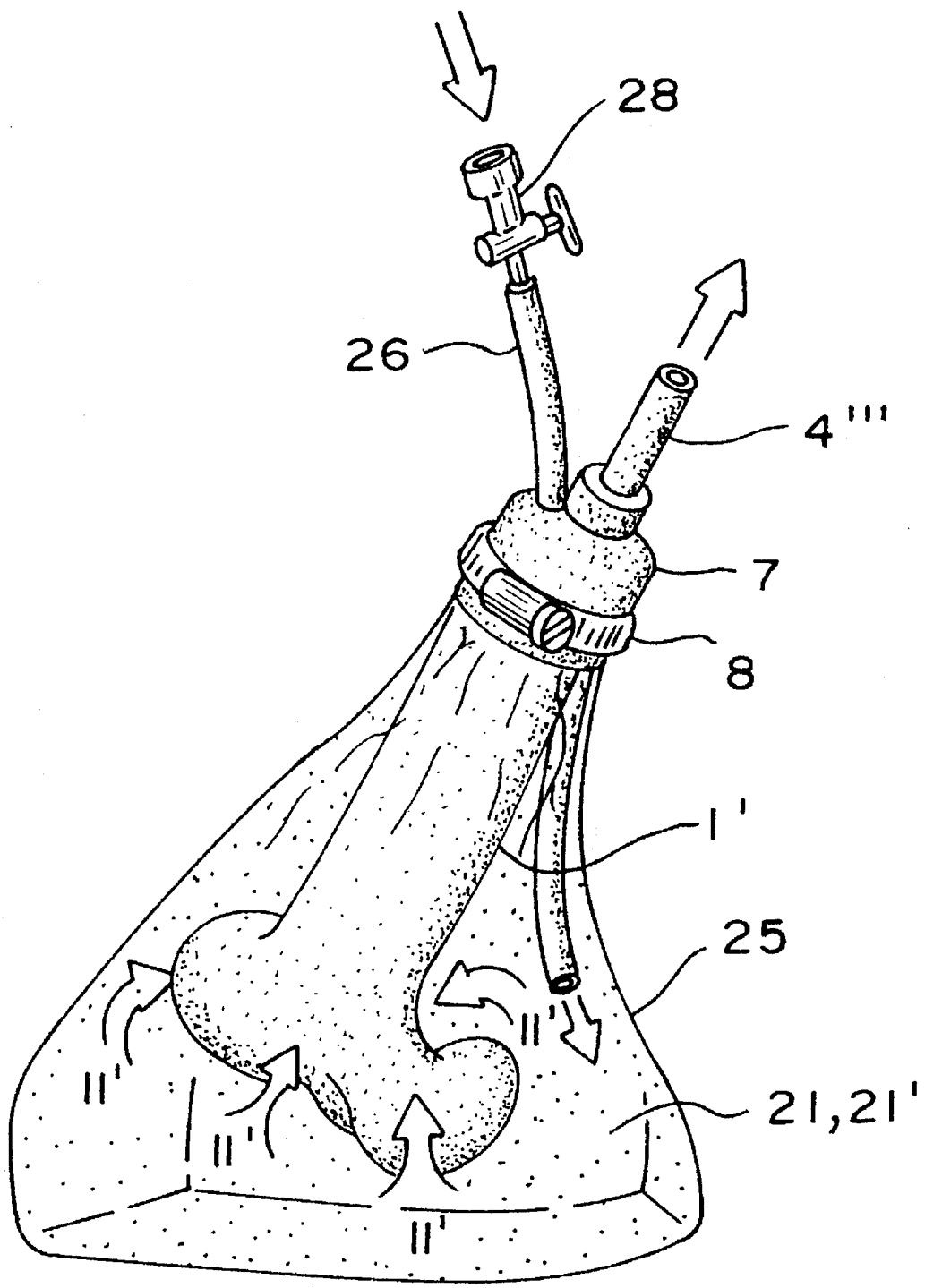
FIG. 5 is a plan view of a large bone graft, e.g. a half femur being processed according to another embodiment of the instant invention.

FIG. 5 is a view of another embodiment of a bone cleaning apparatus and method. Those components which are the same as in the previous embodiments have been labelled with the same reference numerals and may not be specifically described with respect to the instant embodiment. As described with regard to the previous embodiments, a large bone is thawed and debrided of excess soft tissue (including the excess cartilage present on the articulating surfaces where desired). Next, the large bone is cut substantially in half approximately midway between its proximal and distal ends, using a bone saw, in the same manner as that described with respect to FIG. 2. The proximal end of the femur is shown in FIG. 5, for example. However, the distal end of the femur, or either half of any of the previously mentioned large bones can be similarly processed. Optionally, pulsatile lavage or mechanical means (e.g., use of currettes, augurs or other mechanical scooping or scraping means), may be used for initial removal of bone marrow from the luminal space, prior to vacuum processing.

A first solution 21 is added to a deformable container 25 and then the bone graft 1' is placed into the deformable container, and is immersed towards the bottom thereof. The deformable container 25 is deformed to exclude as much air as possible, and is carefully folded around and near the cut end of the bone graft 1'. Then a sealing cap 7 is placed over the cut end of the bone graft 1' and the deformable container 25, and secured with a clamping device 8. The vacuum line 4 is attached securely to the access line 4''' in the sealing cap.

The temperature of the cleaning solution may be adjusted prior to addition of the bone graft 1'. The deformable container 25 with the bone graft 1' may further be placed into a container of sterile, temperature controlled water. Vacuum is then applied to the system via vacuum line 4 and the flow rate of solution through the bone graft is maintained as specifically discussed with the previous embodiments. Procedures for drawing of the first solution 21, refilling with the first solution 21', when necessary, and changing over to the second solution are the same as those discussed previously with regard to the embodiment shown in FIG. 3.

EXAMPLES

The following examples illustrate processing of large bone grafts according to the instant invention.

Example I

A femur was thawed, debrided of excess soft tissue (including the excess cartilage present on the articulating surfaces) and a hole approximately ¼ to ⅝ inch outside diameter was drilled in the bone shaft approximately midway between the distal and proximal ends of the bone. The hole was only drilled deep enough to penetrate the cortical bone so that intramedullary bone marrow could be flushed from the bone and so the tapping port could be securely inserted into the hole. The vacuum line was attached securely to the tapping port. Two liters of a solution of 10% ethanol in a 0.01X solution containing 0.0066 weight percent Brij-35, 0.002 weight percent Nonidet P-40, and 0.002 weight percent Nonoxynol-9 in endotoxin free water were added to an open container in a clean room environment under sterile conditions. The femur having the vacuum line attached via the tapping port was then placed into the container, and immersed towards the bottom of the container.

The temperature of the cleaning solution was adjusted to 45° C. prior to addition of the bone graft. A vacuum was applied to the system and maintained in the range of 25 to 27 mm Hg. The flow rate of solution through the bone graft was maintained at approximately 10 ml per minute by adjusting the vacuum. The solution collected in the disposable container was dark red initially, turning to a color similar to that of serum as bone marrow was removed from the graft. By sampling the effluent material being removed from the bone graft, via a sampling port accessible by use of a syringe, it was possible to monitor completion of bone marrow removal by measuring absorbance at 410 nm, to determine when essentially all of the bone marrow was removed from the bone graft. After drawing two liters of first solution through the bone graft, the vacuum to the system was discontinued and the open container was refilled with one liter of endotoxin-free deionized/distilled water. The vacuum was reapplied to the system. The deionized/distilled water was flushed through the bone graft at approximately 15 ml per minute to remove the detergent solution. Following the flushing of detergent solution from the bone graft, vacuum was discontinued to the system and the bone graft was removed from the open container, after which the vacuum line and tapping port were removed. The bone graft was then ready for further processing into small bone grafts as required.

Example II

A femur was thawed, debrided of excess soft tissue (including the excess cartilage present on the articulating surfaces where desired) and cut in half using a bone saw. The proximal end of the femur was used in this example, however, the distal end of the femur would be similarly processed. Pulsavac lavage was applied to remove bone marrow from the luminal space. One liter of a solution of 10% ethanol in a 0.01X solution containing 0.0066 weight percent Brij-35, 0.002 weight percent Nonidet P-40, and 0.002 weight percent Nonoxynol-9 in endotoxin free water was added to an open container in a clean room environment under sterile conditions. A sealing cap was placed over the cut end of the bone graft and secured using a clamping device. A vacuum line was attached securely to an access line in the sealing cap.

The bone graft having the vacuum line attached via the Pansealing cap and access line was then placed into the container, and immersed towards the bottom of the container. The temperature of the cleaning solution was adjusted to room temperature (approximately 27° C.) prior to addition of the bone graft. Vacuum was applied to the system and maintained in the range of about 25 to 27 mm Hg. The flow rate of solution through the bone graft was maintained at approximately 10 ml per minute by adjusting the vacuum.

The solution collected in the disposable container was initially dark red, and turned to a color similar to that of serum as bone marrow was removed from the graft. By sampling the effluent material being removed from the bone graft, via a sampling port accessible by use of a syringe, it was possible to monitor completion of bone marrow removal by monitoring absorbance at 410 nm, and it was possible to determine when essentially all of the bone marrow was removed from the bone graft.

After drawing one liter of first solution through the bone graft, the vacuum to the system was discontinued and the open container was refilled with one liter of endotoxin-free deionized/distilled water (second solution), after which vacuum was reapplied to the system. The deionized/distilled water was flushed through the bone graft at approximately 15 ml per minute to remove the detergent solution. Following the flushing of detergent solution from the bone graft, vacuum was discontinued to the system and the bone graft was removed from the container. Next, the sealing cap and vacuum line were removed. The bone graft was then ready for further processing into small bone grafts as required.

Example III

A femur was thawed, debrided of excess soft tissue (including the excess cartilage present on the articulating surfaces) and a hole approximately ¼ to ⅝ inch outside diameter was drilled in the bone shaft approximately midway between the distal and proximal ends of the bone. The hole was only drilled deep enough to penetrate the cortical bone such that intramedullary bone marrow could be removed where possible, and a tapping port could be securely inserted into the hole. A vacuum line was attached securely to the tapping port. Two liters of a solution of 10% ethanol in a 0.01X solution containing 0.0066 weight percent Brij-35, 0.002 weight percent Nonidet P-40, and 0.002 weight percent Nonoxynol-9 in endotoxin free water were added to a deformable container designed to hold approximately 3 liters and the bone graft with attached vacuum line was placed into the container and immersed towards the bottom of the container. The deformable container was deformed to exclude as much air as possible and the container was tightly sealed around the vacuum line using a plastic or elastic clamping device.

The temperature of the cleaning solution was adjusted to 45° C. prior to addition of the bone graft and the deformable container with bone graft were placed into a heated water bath, which was also maintained at 45° C. A vacuum was applied to the system at around 25 to 27 mm Hg. The flow rate of solution through the bone graft was maintained at approximately 10 ml per minute by adjusting the vacuum. The solution collected in the disposable container was initially dark red and eventually turned to a color similar to that of serum as bone marrow was removed from the graft.

By sampling the effluent material being removed from the bone graft, via a sampling port accessible by use of a syringe, it was possible to monitor completion of bone marrow removal by measuring absorbance at 410 nm. It was therefore possible to determine when essentially all of the bone marrow was removed from the bone graft. After drawing two liters of first solution through the bone graft, the vacuum to the system was discontinued and the deformable container was refilled with one liter of endotoxin-free deionized/distilled water (second solution) and a vacuum was reapplied to the system. The deionized/distilled water was flushed through the bone graft at approximately 15 ml per minute to remove the detergent solution. Following the flushing of detergent solution from the bone graft, the vacuum was discontinued to the system and the bone graft was removed from the deformable container, after which the vacuum line and tapping port were removed. The bone graft was then ready for further processing into small bone grafts as required.

Example IV

A femur was thawed, debrided of excess soft tissue (including the excess cartilage present on the articulating surfaces where desired) and cut in half using a bone saw. The proximal end of the femur was used in this example, however, the distal end of the femur would be similarly processed. Pulsavac lavage was applied to remove bone marrow from the luminal space. One liter of a solution of 10% ethanol in a 0.01X solution containing 0.0066 weight percent Brij-35, 0.002 weight percent Nonidet P-40, and 0.002 weight percent Nonoxynol-9 in endotoxin free water was added to a deformable container designed to hold approximately 1.5 liters, and the bone graft was placed into the container and immersed towards the bottom of the container. The deformable container was deformed to exclude as much air as possible, carefully folded around and near the cut end of the proximal femur and then a sealing cap was placed over the cut end of the proximal femur and deformable container and secured using a clamping device.

The vacuum line was attached securely to the access line in the sealing cap. The temperature of the cleaning solution was adjusted to room temperature (approximately 27° C. prior to addition of the bone graft) and the deformable container with bone graft was placed into a container of sterile water. Vacuum was applied to the system and maintained in the range of about 25 to 27 mm Hg. The flow rate of solution through the bone graft was maintained at approximately 10 ml per minute by adjusting the vacuum.

The solution collected in the disposable container was initially dark red, and turned to a color similar to that of serum as bone marrow was removed from the graft. By sampling the effluent material being removed from the bone graft, via a sampling port accessible by use of a syringe, it was possible to monitor completion of bone marrow removal by monitoring absorbance at 410 nm, and it was possible to determine when essentially all of the bone marrow was removed from the bone graft.

After drawing one liter of first solution through the bone graft, the vacuum to the system was discontinued and the deformable container was refilled with one liter of endotoxin-free deionized/distilled water (second solution) and vacuum was reapplied to the system. The deionized/distilled water was flushed through the bone graft at approximately 15 ml per minute to remove the detergent solution. Following the flushing of detergent solution from the bone graft, vacuum was discontinued to the system and the bone graft was removed from the deformable container. Next, the vacuum line and tapping port were removed. The bone graft was then ready for further processing into small bone grafts as required.

Although the invention has been described with reference to particular means, materials and embodiments, it is to be understood that the invention is not limited to the particulars disclosed and extends to all equivalents within the scope of the claims.

What is claimed:

1. A process for cleaning large bone grafts, comprising:
   selecting a large substantially intact bone;
   removing excess cartilage from at least one articulating surface of the bone;
   preparing an opening through the cortical layer of the bone to permit access of a vacuum line to the bone cavity;
   attaching a vacuum line via the opening for application of vacuum to the bone cavity;
   immersing the bone in a solution within a container wherein the solution includes at least one solvent for bone marrow; and
   applying a vacuum to the vacuum line to draw the solution through the at least one cartilaginous articulating surface and then through the bone cavity so as to draw the solution and solubilized bone marrow through the vacuum line to exit the bone at the opening.

2. The process according to claim 1, further comprising:
   sealing the opening prior to immersing the bone in the solution.

3. The process according to claim 1, further comprising:
   sealing the opening after immersing the bone in the solution.

4. The process according to claim 1, further comprising:
   discontinuing the application of vacuum when the bone has been substantially cleaned of bone marrow.

5. The process according to claim 1, further comprising:
   refilling the container with a second solution for further processing the bone including flushing the first solution from the bone; and
   drawing the second solution through the at least one cartilaginous articulating surface and then through the bone cavity and the vacuum line to exit the bone at the opening.

6. The process according to claim 5, wherein the second solution comprises a washing solution for flushing the first solution from the bone and for further reducing bacterial, fungal or viral contaminants.

7. The process according to claim 6, wherein the washing solution comprises at least one component selected from the group consisting of endotoxin-free deionized/distilled water and ethanol.

8. The process according to claim 7, wherein the washing solution further comprises at least one component selected from the group consisting of antibiotics, antiviral agents, hydrogen peroxide, permeation enhancers, organic acids and dilute solutions of strong acids.

9. The process according to claim 1, further comprising collecting the solution drawn through the bone cavity via the vacuum into a disposable container.

10. The process according to claim 9, further comprising adding at least one strong viral or bacterial inactivator to the disposable container prior to receiving solutions therein.

11. The process according to claim 1, further comprising providing at least one filter in the vacuum line to further prevent potential spread of biohazardous materials.

12. The process according to claim 1, wherein the preparing an opening through the cortical layer comprises drilling a hole through the cortical layer and sealing a tapping port therein; and
    the attaching the vacuum line via the opening for application of vacuum to the bone cavity comprises securely attaching one end of the vacuum line to the tapping port so as to seal the vacuum line with the cortical bone opening.

13. The process according to claim 12, wherein the container of solution comprises a deformable container and, after submersing the bone in the deformable container of solution, the process further comprising tightly sealing the deformable container around the vacuum line or point of attachment of the vacuum line to the bone.

14. The process according to claim 13, further comprising:
    immersing the deformable container of solution which contains the bone into a temperature controlled water bath.

15. The process according to claim 1, wherein the preparing an opening through the cortical layer comprises cutting the bone transversely between proximal and distal ends;
    the process further comprising placing and sealing a sealing cap over the cut end of the bone; and
    the attaching the vacuum line via the opening for application of vacuum to the bone cavity comprises securely attaching one end of the vacuum line to the sealing cap.

16. The process according to claim 15, further comprising:
    initial removal of bone marrow from the cut end of the luminal space of the bone, using pulsatile lavage, prior to the steps of sealing the opening and attaching the vacuum line.

17. The process according to claim 15, further comprising:
    initial removal of bone marrow from the cut end of the luminal space of the bone, using mechanical means, prior to the steps of sealing the opening and attaching the vacuum line.

18. The process according to claim 1, further comprising adjusting the level of the applied vacuum to maintain solvent flow through the bone of from about 8 ml/min to 32 ml/min.

19. The process according to claim 18, wherein the level of the applied vacuum is adjusted to maintain solvent flow through the bone of from about 15 ml/min to 25 ml/min.

20. The process according to claim 1, wherein the solution comprises endotoxin-free deionized/distilled water and at least one solvent selected from the group consisting of anionic detergents and non-anionic detergents.

21. The process according to claim 20, wherein the solution further comprises ethanol.

22. The process according to claim 20, wherein the solution comprises at least one solvent selected from the group consisting of polyoxyethylene alcohols, polyethylene glycol p-isooctylphenylethers, polyoxyethylene nonylphenol, and polyoxyethylene sorbitol esters.

23. The process according to claim 20, wherein the solution further comprises at least one component selected from the group consisting of antibiotics, antiviral agents, hydrogen peroxide, permeation enhancers, organic acids and dilute solutions of strong acids.

24. The process according to claim 1, wherein the solution comprises about 0.0001X to 10X of a 1X detergent solution containing about 0.066 weight percent Brij-35, about 0.02 weight percent Nonidet P-40, and about 0.02 weight percent Nonoxynol-9 in endotoxin free water.

25. The process according to claim 24, wherein the solution comprises about 0.001X to 0.1X of the 1X detergent solution.

26. The process according to claim 25, wherein the solution comprises about 0.001X to 0.01X of the 1X detergent solution.

27. The process according to claim 26, wherein the solution comprises about 0.005X to 0.01X of the 1X detergent solution.

28. The process according to claim 1, wherein the solution comprises about 5 to 95% ethanol, measured by a volume-to-volume ratio.

29. The process according to claim 28, wherein the solution comprises about 10 to 30% ethanol, measured by a volume-to-volume ratio.

30. The process according to claim 1, wherein the solution comprises endotoxin-free deionized/distilled water and at least one detergent selected from the group consisting of anionic detergents and nonanionic detergents, in concentrations ranging from about 0.001 to 2 weight percent.

31. The process according to claim 30, wherein the solution further comprises ethanol.

32. The process according to claim 30, wherein the solution comprises at least one solvent selected from the group consisting of polyoxyethylene alcohols, polyethylene glycol p-isooctylphenylethers, polyoxyethylene nonylphenol, and polyoxyethylene sorbitol esters.

33. The process according to claim 30, wherein detergent concentration ranges from about 0.01 to 0.5 weight percent.

34. The process according to claim 1, wherein the solution is controlled within a temperature range of about 20° C. to 65° C. and maintained within the temperature range during processing.

35. The process according to claim 34, wherein the temperature range is controlled and maintained at about 27° C. to 55° C.

36. The process according to claim 35, wherein the temperature range is controlled and maintained at about 40° C. to 48° C.

37. The process according to claim 1, further comprising:
monitoring the solution exiting the bone cavity to determine when essentially all of the bone marrow has been removed from the bone.

38. The process according to claim 37, wherein the monitoring comprises measuring absorbance in the range of about 410 nm to 700 nm.

39. The process according to claim 38, wherein the monitoring comprises measuring absorbance at substantially 410 nm.

40. The process according to claim 37, wherein the monitoring comprises a visual monitoring of the color of the solution exiting the bone.

41. The process according to claim 1, wherein:
the solution comprises a first solution comprising about 0.01X of a 1X detergent solution containing about 0.066 weight percent Brij-35, about 0.02 weight percent Nonidet P-40, and about 0.02 weight percent Nonoxynol-9 in endotoxin free water;
refilling the container with a second solution for further processing the bone including flushing the first solution from the bone; and
drawing the second solution through the at least one cartilaginous articulating surface and then through the bone cavity and the vacuum line to exit the bone at the opening so that a maximum concentration of solution in the bone is equivalent to 0.001X detergent solution.

42. A bone graft produced by the process recited in claim 41.

43. A bone graft produced by the process recited in claim 1.

44. A process for cleaning large bone grafts, comprising:
selecting a large, substantially intact bone;
removing excess cartilage from at least one articulating surface of the bone;
preparing an opening through the cortical layer of the bone by cutting the bone transversely between proximal and distal ends to permit access of a vacuum line to the bone cavity;
immersing the bone in a deformable container of solution which contains at least one solvent for bone marrow;
deforming ends of the deformable container around the cortical surface near the cut end of the bone;
sealing the opening by placing and sealing a sealing cap over the cut end of the bone and the ends of the deformable container;
attaching a vacuum line via the opening for application of vacuum to the bone cavity by securely attaching one end of the vacuum line to the sealing cap;
applying a vacuum through the vacuum line to draw the solution through the at least one cartilaginous articulating surface and then through the bone cavity so as to draw the solution and solubilized bone marrow through the vacuum line to exit the bone at the opening; and
discontinuing the application of vacuum when the bone has been substantially cleaned of bone marrow.

45. The process according to claim 44, further comprising:
refilling the deformable container with a second solution for further processing the bone including flushing the first solution from the bone; and
drawing the second solution through the at least one cartilaginous articulating surface and then through the bone cavity and the vacuum line to exit the bone at the opening.

46. The process according to claim 44, further comprising collecting the solution drawn through the bone cavity via the vacuum into a disposable container.

47. The process according to claim 46, further comprising adding at least one strong viral or bacterial inactivator to the disposable container prior to receiving solutions therein.

48. The process according to claim 44, further comprising providing at least one filter in the vacuum line to further prevent the potential spread of biohazardous materials.

49. The process according to claim 44, further comprising:

initial removal of bone marrow from the cut end of the luminal space of the bone, using pulsatile lavage, prior to the steps of sealing the opening and attaching the vacuum line.

50. The process according to claim 44, further comprising:

initial removal of bone marrow from the cut end of the luminal space of the bone, using mechanical means, prior to the steps of sealing the opening and attaching the vacuum line.

51. The process according to claim 44, further comprising:

immersing the deformable container of solution which contains the bone, into a temperature controlled water bath, after attachment of the vacuum line.

52. The process according to claim 44, wherein the solution comprises about 0.0001X to 10X of a 1X detergent solution containing about 0.066 weight percent Brij-35, about 0.02 weight percent Nonidet P-40, and about 0.02 weight percent Nonoxynol-9 in endotoxin free water.

53. The process according to claim 52, wherein the solution comprises about 0.001X to 0.1X of the 1X detergent solution.

54. The process according to claim 53, wherein the solution comprises about 0.001X to 0.01X of the 1X detergent solution.

55. The process according to claim 54, wherein the solution comprises about 0.005X to 0.01X of the 1X detergent solution.

56. The process according to claim 44, wherein:

the solution comprises a first solution comprising about 0.01X of a 1X detergent solution containing about 0.066 weight percent Brij-35, about 0.02 weight percent Nonidet P-40, and about 0.02 weight percent Nonoxynol-9 in endotoxin free water;

refilling the container with a second solution for further processing the bone including flushing the first solution from the bone; and drawing the second solution through the at least one cartilaginous articulating surface and then through the bone cavity and the vacuum line to exit the bone at the opening so that a maximum concentration of solution in the bone is equivalent to 0.001X detergent solution.

57. A bone graft produced by the process recited in claim 44.

58. A bone graft produced by the process recited in claim 56.

* * * * *